United States Patent
O'Hora et al.

(10) Patent No.: US 9,289,277 B2
(45) Date of Patent: Mar. 22, 2016

(54) DENTAL ATTACHMENT APPLIANCE AND DEVICE

(71) Applicants: Michael J. O'Hora, Phelps, NY (US); William P. O'Hora, Waterloo, NY (US)

(72) Inventors: Michael J. O'Hora, Phelps, NY (US); William P. O'Hora, Waterloo, NY (US)

(*) Notice: Subject to any disclaimer, the term of this patent is extended or adjusted under 35 U.S.C. 154(b) by 0 days.

(21) Appl. No.: 13/927,403

(22) Filed: Jun. 26, 2013

(65) Prior Publication Data
US 2015/0004562 A1    Jan. 1, 2015

(51) Int. Cl.
*A61C 13/00* (2006.01)
*A61C 13/265* (2006.01)
*A61C 13/271* (2006.01)
*A61C 13/277* (2006.01)

(52) U.S. Cl.
CPC ............ *A61C 13/2656* (2013.01); *A61C 13/26* (2013.01); *A61C 13/277* (2013.01)

(58) Field of Classification Search
CPC ..................................................... A61C 13/277
USPC .................................. 433/180–183, 190–195
See application file for complete search history.

(56) References Cited

U.S. PATENT DOCUMENTS

| | | | |
|---|---|---|---|
| 3,216,111 A | 11/1965 | Sink | |
| 3,530,582 A | 9/1970 | Weissman | |
| 3,787,975 A * | 1/1974 | Zuest | 433/182 |
| 4,571,185 A * | 2/1986 | Rota | 433/173 |
| 4,768,957 A | 9/1988 | Segura | |
| 4,917,608 A | 4/1990 | Smith | |
| 5,417,570 A * | 5/1995 | Zuest et al. | 433/177 |
| 6,299,447 B1 * | 10/2001 | Zuest et al. | 433/172 |
| 6,986,660 B2 | 1/2006 | Kumar et al. | |

FOREIGN PATENT DOCUMENTS

EP        0263 235        *  4/1987

* cited by examiner

*Primary Examiner* — Ralph Lewis
(74) *Attorney, Agent, or Firm* — James G. Passé; Passé Intellectual Property, LLC

(57) ABSTRACT

The present invention is an artificial tooth with a device for attaching it to a patient's real tooth, in a position next to the real tooth. The device allows for attachment without the installation of any device in the patient's real tooth. Rather, only a dimple is drilled into the patient's tooth for accepting the device. In one embodiment there is a device on either side of the artificial tooth for installation to a tooth on either side of the artificial tooth.

6 Claims, 2 Drawing Sheets

DENTAL ATTACHMENT APPLIANCE AND DEVICE

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to an attachment device and dental appliance attachment. In particular, it relates to a device for use with the attachment of a dental prosthetic appliance to surrounding teeth.

2. Description of Related Art

The attachment of a prosthetic tooth dental appliance after loss of a tooth has long been a staple of the dental practice. One method has been to fashion a removable denture which is held in place by denture paste or by a tight fit. Where a single or small number of teeth are lost in a single position, the remaining surrounding teeth are often utilized as an attachment point for anchoring the prosthetic tooth or teeth.

The most common method of dental prosthetic device attachment is to fashion a bridge which attaches to a remaining tooth or teeth to provide a rigid connection between the natural teeth and the appliance. These types of devices require a great deal of time to fashion the attachment on the natural teeth and often require multiple fittings. Where the dental appliance needs to be removed or changed, further detailed labor is required and serious damage can occur with the natural teeth.

Other types of connections between a prosthetic tooth and a natural tooth have been attempted as well including locking pin type structures, screws and pistons. Once again, each of these suffers from high cost as well as difficulty in installing and/or removing the appliance and jaw problems due to rigid attachment to the natural tooth due to cranial bone movement.

There is still a serious need to find an appliance attachment means which can easily be installed and removed, is cost effective to build and use, and holds a dental appliance in place during daily use.

BRIEF SUMMARY OF THE INVENTION

The present invention results in the surprising discovery that by using a ball bearing in a sleeve and attaching that to the prosthesis and having a receiving dimple in the natural tooth the above problems and many others in attaching the tooth appliance to a natural tooth or to a fixed artificial tooth for that matter.

Accordingly, the present invention relates to a device for attaching a prosthetic tooth to a user's tooth having a corresponding receiving dimple comprising:
  a) a ball bearing mounted in a circular nylon sleeve wherein the ball bearing protrudes by at least 10% of its diameter;
  b) a structure for securing the sleeve mounted ball bearing in the prosthetic tooth such that only the protruding portion of the ball bearing protrudes from a surface of the prosthetic tooth and positions the ball bearing to mate with the receiving dimple for attachment to the user's tooth.

In another embodiment, the present invention relates to a prosthetic tooth system installed in a patients mouth at a position of a missing tooth comprising:
  a) a user's tooth having a receiving dimple placed on a side of the tooth facing the missing tooth position;
  b) a prosthetic tooth having an attachment device associated with the tooth comprising;
    i. a ball bearing mounted in a circular nylon sleeve wherein the ball bearing protrudes by at least 10% of its diameter;
    ii. a structure for securing the sleeve mounted ball bearing in the prosthetic tooth such that only the protruding portion of the ball bearing protrudes from a surface of the artificial tooth.
  c) wherein the prosthetic tooth has been positioned in the patient's mouth at the position of the missing tooth and the attachment device associated with the tooth such that the protruding portion of the ball bearing is positioned in the patient's tooth receiving dimple to hold the prosthetic tooth in place.

DETAILED DESCRIPTION OF THE INVENTION

Figure 1:
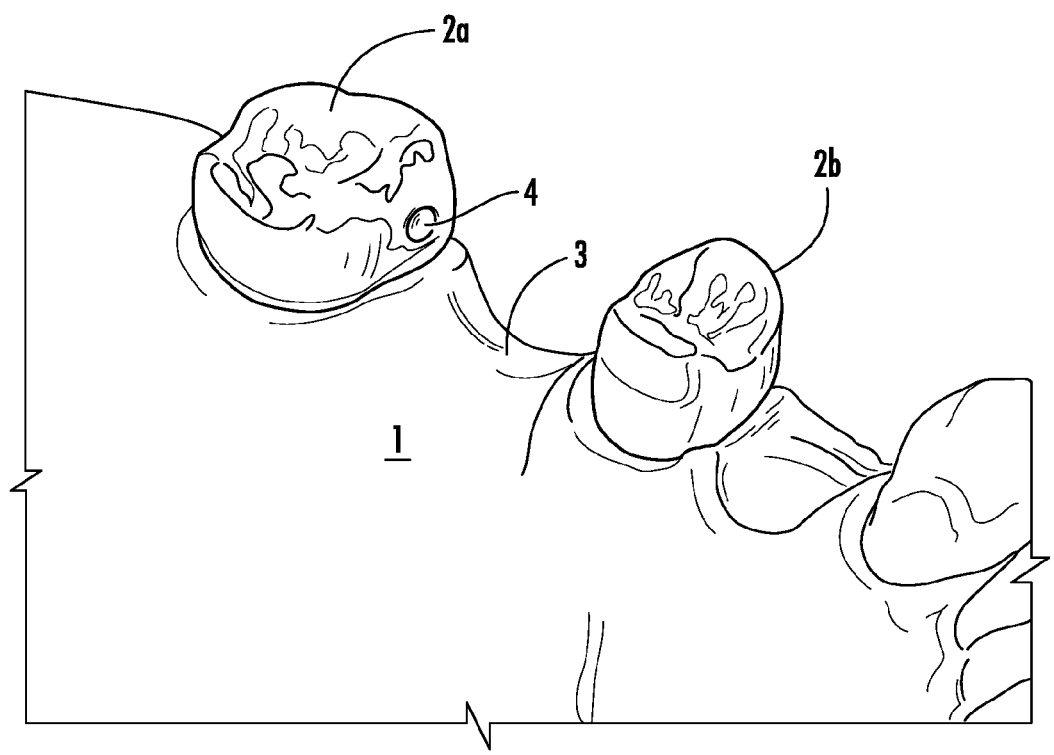
FIG. 1 is a user's tooth with a receiving dimple

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

DEFINITIONS

The terms "about" and "essentially" mean ±10 percent.

The terms "a" or "an", as used herein, are defined as one or as more than one.

The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "prosthetic tooth" refers to one or more artificial teeth designed to be inserted into a patient's mouth in a location where a tooth has previously been removed in the present invention. Where there is more than one tooth, the multiple teeth can be manufactured to be attached to one another permanently or can be independent teeth. The prosthetic tooth can be made of any material normally utilized to make a prosthetic tooth to be inserted into the mouth of a patient. Prosthetic teeth are, by themselves, well known in the art and constructing one that fits the user's open space can easily done by one of average skill in the art.

As used herein the term "user's tooth" refers to an organic original tooth in a user or patient's mouth or a previously permanently or semi-permanently mounted artificial tooth other than the prosthetic tooth of the present invention. The user's tooth will have a receiving dimple which is a depression designed to receive the ball bearing of the attaching device of the present invention. The user's tooth will be a tooth positioned right next to the open space (where there is one or more missing teeth) the prosthetic tooth of the invention is being installed into and the receiving dimple will face that open space at a height to match the ball bearing when the prosthetic tooth of the present invention is mounted in place in the user.

As used herein the term "attaching device for attaching a prosthetic tooth to a user's tooth" refers to a novel connection device for easily installing a prosthetic tooth and where the tooth is necessary to be removed it can easily be removed because of the construction and design of the attaching device. In the present invention, the attaching device is mounted in the prosthetic tooth in a permanent or semi-permanent manner and attaches to the user's tooth via a ball bearing snapping into place in a receiving dimple of the users tooth. The attaching device consists of a ball bearing (of a size about 0.5 mm to about 1.75 mm or as needed) mounted in a circular nylon (medical grade) sleeve wherein the ball bearing protrudes by at least 10% to as much as 80% of its diameter from the nylon sleeve. Together in one embodiment the bearing and sleave are about 1.5-2.5 mm in width. There must be a structure for securing the sleeve mounted ball bearing in the prosthetic tooth such that only the protruding portion of the ball bearing protrudes from the surface of the prosthetic tooth that faces the receiving dimple. This can be part of the nylon sleeve out surface or the nylon sleeve can have an additional attached device for attachment of the attaching device to the prosthetic tooth. In one embodiment it is one or more ridged surface which increases surface area. The device can be glued or cemented into the prosthetic tooth using means know in the art for such attachment.

In one embodiment of the present invention the prosthetic tooth can have one attachment device on either side of the prosthetic tooth such that it can attach to receiving dimples in user's teeth that are positioned on either side of the space the prosthetic tooth will fit into. The prosthetic tooth with the device attached will merely snap into place by press fitting by hand. Positioning the tooth in place and pressing the attachment device ball bearing into the receiving dimple until it snaps in place, the prosthetic tooth is held in place by the form fitting nature of a prosthetic tooth and the ball bearing fit into the receiving dimple. The actual use of the invention will be clearly seen from the examples in the drawings and their descriptions.

Now referring to the drawings, FIG. 1 is a user's tooth with a receiving dimple. A patient or user's jaw 1 is shown. The jaw 1 has natural teeth 2*a* and 2*b* with a space 3 where previously there was a user's tooth that now has been removed. User's tooth 2*a* has receiving dimple 4 which faces space 3 in preparation for receiving a prosthetic tooth of the present invention.

Figure 2:
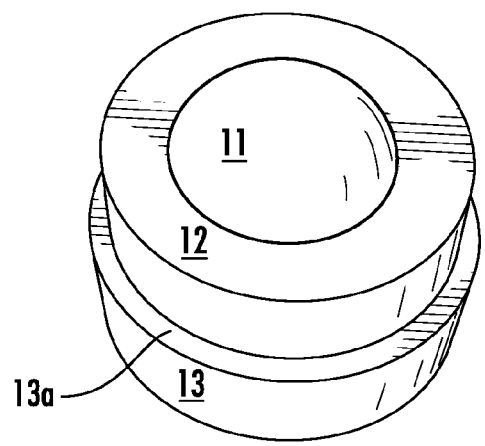
FIG. 2 is a prosthetic tooth attachment device.

FIG. 2 is a prosthetic tooth attachment device which is not yet mounted in a prosthetic tooth. It comprises a ball bearing 11 which protrudes about 40 to 50% in this example from nylon sleeve 12. The attachment device has an attachment surface 13 including high surface ledge 13*a* for creating resistance to the device being pulled loose from a prosthetic tooth.

Figure 3:
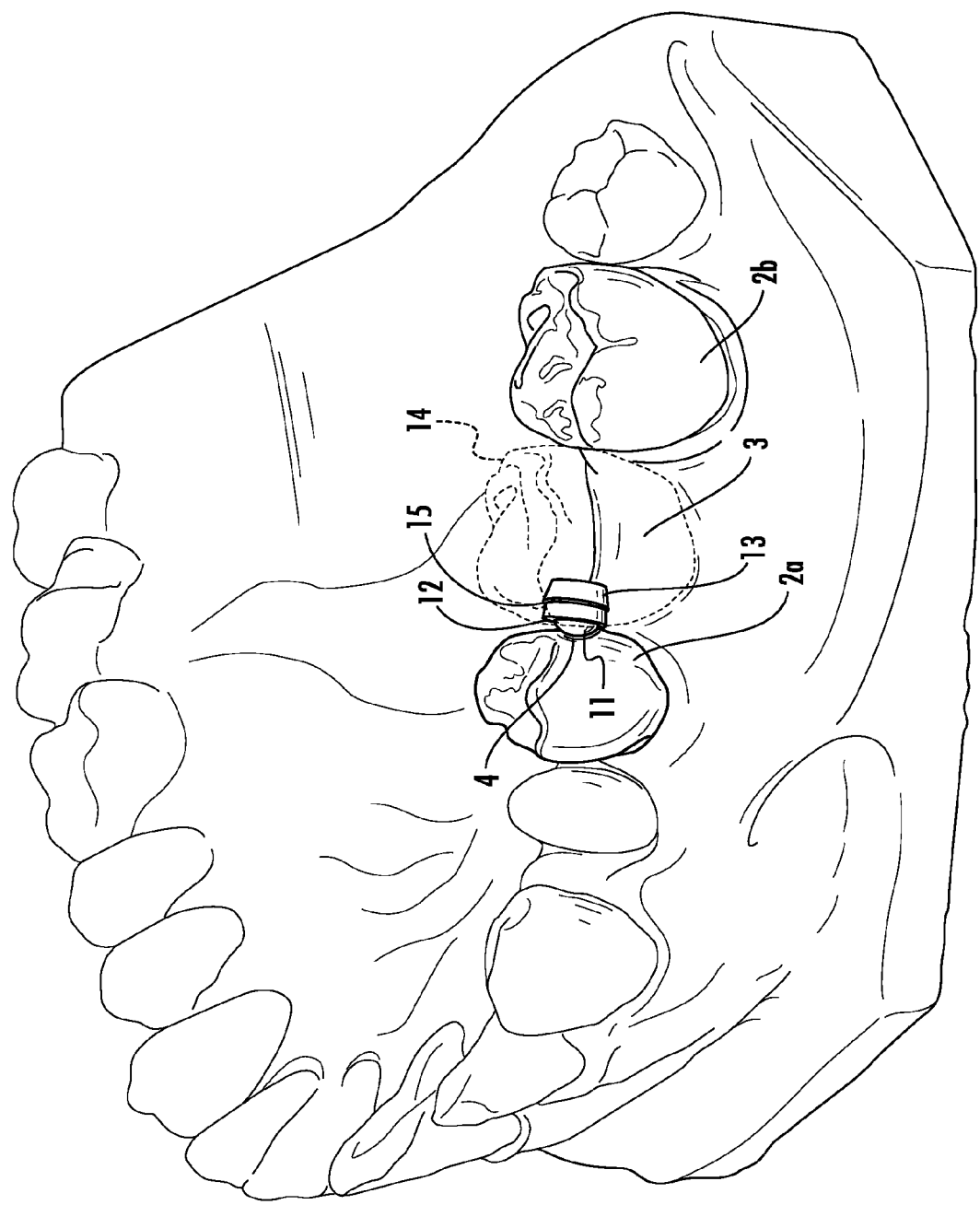
FIG. 3 is a system of the prosthetic tooth with attachment device installed in an open space in user's mouth.

FIG. 3 is a system of the prosthetic tooth with attachment device installed in an open space in user's mouth. In this view the attachment device 15 is shown mounted in prosthetic tooth 14 (shown in dotted line transparent fashion so one can see the placement of the attachment device 15). In this embodiment only one attachment device is utilized however one on either side of prosthetic tooth 14 could have been utilized. The dental professional can determine this type of situation since each tooth replacement has different situational needs in terms of strength of holding a prosthetic tooth in place as well as the structure of the user area around the missing tooth.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. A device for attaching a prosthetic tooth at a position of a missing tooth next to an existing patient's tooth, directly to a ball-shaped dimple drilled in the side of the existing patient's tooth facing the position of the missing tooth that is positioned without any device in the existing patient's tooth for receiving the prosthetic tooth comprising:
   a) a ball bearing adapted to fit within the ball-shaped dimple mounted in a circular nylon sleeve wherein the ball bearing protrudes by at least 10% of its diameter; and
   b) the nylon sleeve adapted for securing the sleeve mounted ball bearing in the side of the prosthetic tooth facing the dimple when the prosthetic tooth is inserted in the position of the missing tooth, such that only the protruding portion of the ball bearing protrudes from a surface of the prosthetic tooth and positions the ball bearing to mate only with the ball-shaped dimple in the patient's tooth.

2. The device according to claim 1 which further comprises a second attachment device according to claim 1 wherein the two devices are adapted to be positioned on opposite sides of the prosthetic tooth.

3. The device according to claim 1 wherein the sleeve has a surface ledge for creating resistance to the device being pulled loose from the prosthetic tooth.

4. The device according to claim 1 wherein the ball bearing protrudes from the sleeve from about 40% to 50%.

5. The device according to claim 1 wherein the device is positioned in the side of a prosthetic tooth for insertion in the space of the missing tooth, with the ball bearing facing the dimple in the existing tooth.

6. A method for attaching a prosthetic tooth at a position of a missing tooth next to an existing patient's tooth, comprising:
  a) drilling a ball-shaped dimple in the side of the existing patient's tooth facing the position of the missing tooth;
  b) selecting a device comprising a ball bearing adapted to fit within the ball-shaped dimple mounted in a circular nylon sleeve, wherein the ball bearing protrudes by at least 10% of its diameter; the nylon sleeve secured in the side of the prosthetic tooth facing the dimple when the prosthetic tooth is inserted in the position of the missing tooth such that only the protruding portion of the ball bearing protrudes from a surface of the prosthetic tooth and positions the ball bearing to mate only with the ball-shaped dimple in the patient's tooth; and
  c) inserting the prosthetic tooth into the space of the missing tooth such that the ball bearing in the side of the prosthetic tooth is positioned within the dimple in the side of the existing patient's tooth sufficient to hold the prosthetic tooth in place.

\* \* \* \* \*